United States Patent [19]

Yoshimura et al.

[11] Patent Number: 5,709,870
[45] Date of Patent: Jan. 20, 1998

[54] ANTIMICROBIAL AGENT

[75] Inventors: Shoji Yoshimura; Hiroyuki Minami, both of Sakai-gun, Japan

[73] Assignee: Rengo Co., Ltd., Osaka, Japan

[21] Appl. No.: 544,532

[22] Filed: Oct. 18, 1995

[30] Foreign Application Priority Data

Oct. 18, 1994 [JP] Japan .................. 6-251939

[51] Int. Cl.$^6$ ........................ A01N 25/08
[52] U.S. Cl. .................. 424/404; 424/405; 424/411; 424/412; 424/413; 424/414; 424/618
[58] Field of Search .............. 424/404, 405–413, 424/421, 618, 414

[56] References Cited

U.S. PATENT DOCUMENTS

| 2,072,808 | 10/1937 | Bley | 424/618 |
|---|---|---|---|
| 4,744,760 | 5/1988 | Molday | 424/3 |
| 5,468,489 | 11/1995 | Sakuma et al. | 424/49 |

FOREIGN PATENT DOCUMENTS 2809244  9/1979  Germany.

*Primary Examiner*—Neil S. Levy
*Attorney, Agent, or Firm*—Nikaido, Marmelstein, Murray & Oram LLP

[57] ABSTRACT

A silver-containing antimicrobial agent which is excellent in affinity to fiber, antimicrobial property, anti-fungus property and stability to heat and light. It comprises carboxymethyl cellulose containing silver in the amount of 0.01 to 1% by weight and having the degree of substitution to carboxymethyl group of not less than 0.4. The carboxymethyl cellulose may be a crosslinked compound to make the antimicrobial agent water resistant.

9 Claims, No Drawings

ANTIMICROBIAL AGENT

The present invention relates to an antimicrobial agent which is applicable to fibrous products, paper, leather and porous material.

As antimicrobial agents applicable to fibrous products, paper, etc., antimicrobial metals such as silver, copper and zinc are known. It is considered that antimicrobial metals exhibit antimicrobial property because when metal ions are absorbed into microbial cells, they inhibit respiration and basal metabolism of electron transfer system and the transport of substrate in cell membrane.

Among antimicrobial metals, silver is a safe metal because silver in metallic state is little absorbed in human body. Thus silver is used as tableware and artificial tooth. In ionic state (e.g. aqueous solution of silver nitrate), it exhibits antimicrobial activity as disinfectant.

But agents in liquid state are troublesome to handle and limited in use. Thus some antimicrobial agents support silver on activated carbon. But such agents cannot continue antimicrobial effect because of too rapid elution of silver ions. Also they had a problem in safety.

Other solid state antimicrobial agents include ones having silver ions supported on zeolite (which is an inorganic ion exchanger) or clay. But such agents can not continue antimicrobial effect because silver ions elute. Also, silver ions supported in the inside of a hard three-dimensional structure of a silicate are difficult to contact microbial cells efficiently and thus are not satisfactory in their function.

As antimicrobial agents supporting silver on an organic compound, agents consisting of a copolymer of styrene monomer and monomer (such as acrylic acid or metacrylic acid exchanged by silver ions) containing carboxyl group are known (unexamined Japanese patent publication 53-109941).

Also, as antimicrobial agents using cellulosic polymers which have affinity with fiber, there are known compositions having sulfadiazine silver and carboxymethylcellulose dispersed in an acrylic adhesive (unexamined Japanese patent publication 2-147063) and sheets containing zeolite ion-exchanged by silver and copper ion and water-absorptive polymer such as carboxymethylcellulose, which keep freshness for leaf vegetable (unexamined Japanese patent publication 3-148470).

But conventional compositions containing silver or silver compound and carboxymethylcellulose will not exhibit antimicrobial property safely and effectively if they do not have predetermined composition. Therefore, such compositions cannot be used as antimicrobial agents, directly mixed or impregnated in fiber or other matrix.

None of conventional silver-containing antimicrobial agents have both of long-lasting antimicrobial activity and affinity with fiber. No antimicrobial agents are available which achieve required sterilization ratio when mixed in paper or fibrous products. Also, antimicrobial agents containing a silver compound in carboxymethylcellulose are liable to change in properties or color due to heat and light.

None of such conventional silver-containing antimicrobial agents achieve a sterilization ratio over 40%, which is the minimum effective value at 12.5 ng/ml of silver (at this concentration, even silver nitrate cannot have antibacterial activity), when measured with the Shake Flask Method stipulated by Association of Antibacterial Treatments for Textiles. Japan (hereinafter referred to as "Shake Flask Method").

An object of the present invention is to provide a silver-containing antimicrobial agent which has good affinity with fiber and such a good antimicrobial property as to meet the antimicrobial requirement and which is stable to heat and light and will not cause the product to change in color or quality.

Another object of the present invention is to provide an antimicrobial agent which has water resistance and thus maintain antimicrobial property in water-contacting environments.

In accordance with the present invention, there is provided an antimicrobial agent which comprises carboxymethylcellulose containing silver in the amount of 0.01 to 1% by weight and having a degree of substitution of carboxymethyl group of not less than 0.4.

The degree of substitution to carboxymethyl group may be 0.4 to 1.

The carboxymethylcellulose in the agent may be a crosslinked compound.

The antimicrobial agent according to the present invention is a silver salt of carboxymethylcellulose (hereinafter referred to as CMC). By limiting its degree of substitution to carboxymethyl group and the silver content to predetermined ranges, the dissociation rate speed of silver ions is suppressed.

Since CMC is a cellulose derivative, silver salts of CMC has good affinity with paper and fiber. Because of flexible structure, it is easy to contact microbial cells. Thus, even if it contains a relatively small amount of silver ions, it will exhibit antibacterial and antifungal properties efficiently. In other words, with the antimicrobial agent of the present invention, the total amount of silver ions necessary to exhibit a sufficient antimicrobial property may be small. Thus, the antimicrobial agent is difficult to be oxidized by visible light, ultraviolet or heat.

Such silver salts of CMC suppress the dissociation of silver ions, provided that they have a degree of substitution to carboxymethyl group in a predetermined range and a relatively small amount of silver. Thus silver salts of CMC have good safety and high, sustaining antimicrobial activity and stability to heat and light. They can provide an excellent antimicrobial agent which is applicable to fiber without any problems.

Crosslinked CMC are insoluble to water and are usable to applications where they contact water. In case that the raw material sodium carboxymethylcellulose (hereinafter abbreviated as CMC(Na) has a higher degree of substitution than 0.4, it is soluble to water. Thus, it is reacted with a crosslinking agent such as epichlorohydrin into a crosslinked form which is insoluble to water.

The CMC used in the present invention is represented by Formula 1 and has a degree of substitution to carboxymethyl group per anhydroglucose (hereinafter abbreviated DS) and its silver content restricted in predetermined ranges. It may be a crosslinked CMC.

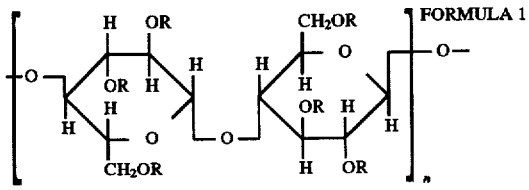

(wherein R is a hydrogen atom or a carboxymethyl group or its silver salt. DS to carboxymethyl group is 0.4 or more. The silver content is 0.01 to 1 weight %. n=100 to 2000)

In case that the silver content in CMC is less than 0.01 wt %, the antimicrobial agent could not achieve the sterilization ratio of over 40% as measured with the Shake Flask Method at the low silver concentration (12.5 ng/ml). In case that the silver content is over 1 wt %, the antimicrobial agent would not exhibit antimicrobial property sufficiently because the silver ions are liable to dissociate. Also, it would be unfavorable in economy and safety.

If CMC has a DS value of less than 0.4, excess carboxyl group to silver would be small in number, so that silver is liable to dissociate from CMC. If CMC has a DS value of over 1.0, CMC would turn from hydrophilic to hydrophobic and would not exhibit the antimicrobial property satisfactorily. Also, the manufacturing process would be complicated particularly in the step of introducing carboxymethyl group. This would affect economy and utility unfavorably.

Provided CMC contains silver as an essential component in the abovementioned content, the antimicrobial agent may contain salts of other metal in such contents as not to inhibit the effect by the present invention. Such metals may be copper or zinc. Alkali metals coexisting with them may be lithium, sodium or potassium. Alkaline earth metals such as calcium may coexist with them. The antimicrobial agent may contain ammonium salts.

Silver salts of CMC (hereinafter abbreviated as CMC (Ag)) may be manufactured by use of sodium salts of CMC(Na). CMC(Na) may be manufactured by etherification, that is, mixing alkaline cellulose and sodium monochloroacetate to dissolve and precipitating with methylalcohol. Also, commercially available CMC(Na) may be used such as sodium cellulose glycolate, Carmellose sodium and sodium carboxymethylcellulose. The degree of polymerization for CMC should be 100 to 2000, more preferably 200 to 1200.

The degree of substitution (DS) to carboxymethyl group was determined with the method described below. It was measured by drying CMC(Na), weighing it, and incinerating at 575° C., titrating the sodium carbonate thus obtained with standard sulfuric acid, and calculating the DS value from the titration value.

CMC(Ag) may be obtained by substituting sodium in CMC(Na) with silver. In case that the CMC(Na) used is water insoluble, it is suspended in water or an aqueous organic solvent. In case that it is water soluble, it is suspended in an aqueous organic solvent. A required amount of silver nitrate is added to the suspended CMC(Na) for substitution. As an aqueous organic solvent, aqueous methanol solution (mixing ratio, water: methanol=2:8) is preferable.

The silver content of the CMC(Ag) obtained was determined by drying the specimen, weighing and incinerating it at 900° C., dissolving the metal silver obtained in a nitric acid solution into a silver nitrate solution, and titrating it with a standard ammonium thiocyanate (Voilhard method). Or atomic absorption spectroscopy was used to determine the silver content.

A water-insoluble CMC(Ag) in the form of crosslinked polymer may be obtained by adding one of the following crosslinking agents to CMC(Na) and crosslinking CMC(Na) in a reaction solvent.

The crosslinking agent may be aldehydes such as formaldehyde, glutaric aldehyde or glyoxal; N-methylol compounds such as dimethylolurea, dimethylolethyleneurea or dimethylol imidazoline; polyhydric carbonic acids such as oxalic acid, maleic acid, butanedioic acid, malic acid or polyacrylic acid; polyhydric epoxy compounds such as ethyleneglycol diglycidyl ether, polyethyleneglycol diglycidyl ether, or diepoxybutane; divinyl compounds such as divinyl sulfone or methylene-bis-acrylamide; polyhydric halogen compounds such as dichloroacetone, dicholoropropanol or dichloroacetic acid; halohydrin compounds such as epichlorohydrin or epibromohydrin.

The molar ratio of crosslinking agent to anhydroglucose should be 0.5 to 3, more preferably 0.7 to 2. As a reaction solvent, a mixture of water and organic solvent may be used with the mixing ratio being about 2:8 (water:organic solvent). As organic solvents, for example, isopropyl alcohol, acetone, ethanol or methanol may be used.

CMC(Ag) in the form of a crosslinked compound may also be manufactured by crosslinking a cellulose and carboxymethylating the crosslinked cellulose. The degree of polymerization of cellulose before crosslinked should be 100 to 2,000. The cellulose may be crosslinked by use of epichlorohydrin at a reaction molar ratio (to anhydroglucose) of 0.7 to 2, using the above described solvents or water only as a reaction solvent. The carboxymethylating may be done with an ordinary solvent method.

The degree of substitution (DS) of the crosslinked CMC (Na) obtained should be not less than 0.4, more preferably 0.4 to 1.0. The degree of swelling to water of the crosslinked CMC(Na) should be small for a practical use. But if the degree of swelling is too large, crosslinking may be repeated.

The antimicrobial agent comprising CMC(Ag) obtained may be used by dissolving or suspending it in a binder, applying the solution obtained to the surface of an equipment to be protected from bacteria or fungus, removing the solvent, thereby forming a coating of CMC (Ag). Or else, it may be used by impregnating the material with it and removing the solvent, or mixing it with wood pulp or cellulose fiber and making paper.

The binder used in coating the agent may be selected according to application and according as whether CMC (Ag) is soluble or insoluble to water. The binders usable include natural polymers or their derivatives such as starch, casein, soybean protein, cellulose acetate, cellulose nitrate, methylcellulose and hydroxyethyl cellulose; synthetic polymers such as polyvinylacetate and its copolymer, polyvinylalcohol, polyvinylacetal, polyacrylate, polyvinylidene chloride, polyethylene and its copolymer, polystyrene-butadiene copolymer, silicone, amino resin, alkyd resin and polyurethane.

The antimicrobial agent according to the present invention may be applied, impregnated or mixed (for making paper) to boards such as corrugated cardboard, white board and separate sheets; cardboard as construction material; cardboard for core board. Also, it may be impregnated in fiber, non-woven fabrics, leather, sponge and wood. Further, it may be used with objects which are not cleaned or uncleanable, such as beddings, tatami (traditional Japanese straw mats), wall paper, wall plate, furniture, porous heat insulating material, filter documents and shoes.

In order to improve or adjust the antimicrobial effect, the antimicrobial agent according to the present invention may be used with an antioxidant, masking agent, ultraviolet absorber, coloring agent, surface-active agent, coupling agent or other additive.

EXAMPLE 1

Preparation of crosslinked CMC(Ag) (DS=0.53, silver content=0.048 wt %)

5.0527 g of crosslinked CMC(Na) (DS=0.53, water content: 12.6 wt %) was suspended in 100 ml of water in a 200 ml graduated flask. A silver nitrate solution ($AgNO_3$:water= 3.35 mg/10 ml) was added to the suspension, which was shaked for 71 hours under light shielded.

The precipitate was filtered with a glass filter, washed with a 50% ethanol and then with a 100% ethanol and dried with $P_2O_5$+silica gel for three days. 4.996 g of white powder crosslinked CMC(Ag) (water content: 10.26 wt %) was obtained.

The silver content of the crosslinked CMC(Ag) obtained was measured with the ammonium thiocyanate determination method.

(Ammonium thiocyanate determination method (Vollhard method))

The specimen was dried, weighed and incinerated at 900° C. The metal silver obtained was dissolved in a nitric solution into silver nitrate solution. It was heated to remove $NO_2$ gas and titrated with standard ammonium thiocyanate with ferric ammonium sulfate added as an indicator.

As a result, in Example 1, the silver content was 0.048 wt % (for anhydride) and 0.043 wt % (for water-containing specimen), and the degree of substitution to silver was 0.001.

EXAMPLE 2

Preparation of crosslinked CMC(Ag) (DS=0.53, silver content=0.048 wt %) by using methanol as a solvent for substitution.

3.5 g of crosslinked CMC(Na) (DS=0.53, water content: 14.71 wt %) was suspended in 60 ml of 80% methanol in a 200 ml graduated flask. A silver nitrate solution ($AgNO_3$: water=2.91 mg/5 ml) was added to the suspension, which was shaken for 135 hours under light shielded.

The precipitate was filtered with a glass filter, washed with a 50% ethanol and then with a 100% ethanol and dried with $P_2O_5$+silica gel for three days. 3.1937 g of crosslinked CMC(Ag) (water content: 6.46 wt %) was obtained.

The silver content of the crosslinked CMC(Ag) obtained was measured with the ammonium thiocyanate determination method.

As a result, the silver content was 0.048 wt % (for anhydride) and 0.045 wt % (for water-containing specimen), and the degree of substitution to silver was 0.0009.

EXAMPLE 3

Preparation of crosslinked CMC(Ag) (DS=0.51, silver content=0.114 wt %)

5.896 g of crosslinked CMC(Na) (DS=0.51, water content: 15.22 wt %) was suspended in 100 ml of 80% methanol in a 200 ml graduated flask. A silver nitrate solution ($AgNO_3$:water=11.47 mg/5 ml) was added to the suspension, which was shaked for 112 hours under light shielded.

The precipitate was filtered with a glass filter, washed with a 50% ethanol and then with a 100% ethanol and dried with $P_2O_5$+silica gel for three days. 5.3370 g of crosslinked CMC(Ag) (water content: 6.82 wt %) was obtained.

The silver content of the crosslinked CMC(Ag) obtained was measured with the ammonium thiocyanate determination method.

As a result, the silver content was 0.114 wt % (for anhydride) and 0.106 wt % (for water-containing specimen), and the degree of substitution to silver was 0.0021.

EXAMPLE 4

Preparation of crosslinked CMC(Ag) (DS=0.6, silver content=0.067 wt %)
1) Synthesis of crosslinked cellulose 21.447 g of cellulose (CF-11, Whatman, n≈200, water content: 6.75 wt %) was suspended in 320 ml of 3% sodium hydroxide. 22.8 g of epichlorohydrin was added to the suspension to react at 50° C. for one hour. The reaction product was filtered, washed with water and then methanol, and air-dried. 20.68 g of crosslinked cellulose (water content: 15.59 wt %) was obtained.

2) Synthesis of crosslinked CMC(Na)

7.9347 g of crosslinked cellulose (water content: 1.68 wt %) was suspended for 30 minutes in a solution containing 4.07 g of sodium hydroxide, 18.53 g of water and 86 ml of isopropyl alcohol (hereinafter abbreviated as IPA). A solution containing 3.94 g of monochloro acetic acid and 8.5 ml of IPA was added and the mixture was stirred at 70° C. for one hour. After reaction, the mixture was filtered while heating and the residue was neutralized with acetic acid in 80% methanol, fully washed with the solvent and dried under reduced pressure. 12.58 g (water content: 12.49 wt %) of crosslinked CMC(Na) was obtained. The ion-exchange capacity was 3.037 meq/g. DS was 0.65.

3) Synthesis of re-crosslinked CMC(Na)

6.0 g of the crosslinked CMC(Na) obtained in step 2) was stirred for one hour in a solution at 83° C. containing 6.1 ml of 4N NaOH, 23 ml of water, 2.27 g of epichlorohydrin and 111 ml of IPA. Then the mixture was neutralized with acetic acid in the same manner as in step 2) and dried with reduced pressure, so that 6.5183 g (water content: 16.39 wt %) of re-crosslinked CMC(Na) was obtained. The ion-exchange capacity was 2.872 meq/g and DS was 0.60.

4) Synthesis of re-crosslinked CMC(Ag)

4.0 g of the re-crosslinked CMC(Na) obtained in step 3) (DS=0.6, water content: 16.39 wt %) was suspended in 70 ml of water in a 200 ml graduated flask. A silver nitrate aqueous solution ($AgNO_3$:water=3.24 mg/10 ml) was added to the suspension and the mixture was shaked for 87 hours under light shielded.

The precipitate was filtered with a glass filter, washed with a 50% ethanol and then with a 100% ethanol and dried with $P_2O_5$+silica gel for three days. 3.7197 g of re-crosslinked CMC(Ag) (water content: 11.55 wt %) was obtained.

The silver content of the crosslinked CMC(Ag) was measured with the ammonium thiocyanate determination method.

The silver content was 0.067 wt % (for anhydride) and 0.059 wt % (for water-containing specimen), and the degree of substitution to silver was 0.0013.

EXAMPLE 5

Preparation of water-soluble CMC(Ag) (DS=0.56, silver content=0.479 wt %)

5.3287 g of CMC(Na) (Tokyo Kasei Kogyo Co., Ltd., DS=0.56, water content: 6.17 wt %, n=1050) was suspended in 50 ml of water in a 200 ml graduated flask. A silver nitrate solution ($AgNO_3$:water=30.6 mg/50 ml) was added to the suspension, which was shaked for 2 hours under light shielded.

The precipitate obtained by adding 3 liters of methanol was filtered with a glass filter, washed with a 100% ethanol and dried with $P_2O_5$+silica gel for three days. 2.5681 g of water-soluble CMC(Ag) (water content: 5.21 wt %) was obtained.

The silver content of the water-soluble CMC(Ag) was measured with the ammonium thiocyanate determination method.

As a result, the silver content was 0.479 wt % (for anhydride) and 0.45 wt % (for water-containing specimen), and the degree of substitution to silver was 0.01.

EXAMPLE 6

Preparation of water-soluble CMC(Ag) (DS=0.56, silver content=0.048 wt %)

53.25 g of CMC(Na) (Tokyo Kasei Kogyo Co., Ltd., DS=0.56, water content: 6.17 wt %) was suspended in 1000 ml of 80% methanol. A silver nitrate solution ($AgNO_3$:water=222.5 mg/25 ml) was added to the suspension, which was shaked for 153 hours under light shielded.

The precipitate was filtered with a glass filter, washed with a 80% ethanol and then with a 100% ethanol and dried with $P_2O_5$+silica gel for three days. 39.116 g of water soluble crosslinked CMC(Ag) (water content: 14.00 wt %) was obtained.

The silver content of the water-soluble CMC(Ag) obtained was measured with the ammonium thiocyanate determination method.

As a result, the silver content was 0.048 wt % (for anhydride) and 0.041 wt % (for water-containing specimen), and the degree of substitution to silver was 0.009.

EXAMPLE 7

Preparation of crosslinked CMC(Ag) (DS=1.35, silver content=0.048 wt %)

12.3061 g of crosslinked CMC(Na) (DS=1.35, water content: 18.74 wt %) was suspended in 200 ml of water. A silver nitrate solution ($AgNO_3$:water=10.68 mg/10 ml) was added to the suspension, which was shaked for 158 hours under light shielded.

The precipitate was filtered with a glass filter, washed with a 50% ethanol and then with a 100% ethanol and dried with $P_2O_5$+silica gel for three days. 11.4479 g of white powder crosslinked CMC(Ag) (water content: 21.35 wt %) was obtained.

The silver content of the crosslinked CMC(Ag) obtained was measured with the ammonium thiocyanate determination method.

As a result, the silver content was 0.048 wt % (for anhydride) and 0.037 wt % (for water-containing specimen), and the degree of substitution to silver was 0.0012.

EXAMPLE 8

Preparation of crosslinked CMC(Ag) (DS=1.35, silver content=0.040.wt %)

4.102 g of crosslinked CMC(Na) (DS=1.35, water content: 18.74 wt %) was suspended in 100 ml of 80% methanol. A silver nitrate solution ($AgNO_3$:water=3.63 mg/1 ml) was added to the suspension, which was shaked for 144 hours under light shielded.

The precipitate was filtered with a glass filter, washed with a 50% ethanol and then with a 100% ethanol and dried with $P_2O_5$+silica gel for three days. 3.5059 g of Crosslinked CMC(Ag) (water content: 6.22 wt %) was obtained.

The silver content of the crosslinked CMC(Ag) obtained was measured with the ammonium thiocyanate determination method.

As a result, the silver content was 0.040 wt % (for anhydride) and 0.037 wt % (for water-containing specimen), and the degree of substitution to silver was 0.001.

EXAMPLE 9

Preparation of crosslinked CMC(Ag) (DS=1.35, silver content=0.115 wt %)

4.171 g of crosslinked CMC(Na) (DS=1.35, water content: 18.74 wt %) was suspended in 100 ml of 80% methanol. A silver nitrate solution ($AgNO_3$:water=7.23 mg/1 ml) was added to the suspension, which was shaked for 95 hours under light shielded.

The precipitate was filtered with a glass filter, washed with a 50% ethanol and then with a 100% ethanol and dried with $P_2O_5$+silica gel for three days. 3.6062 g of white powder crosslinked CMC(Ag) (water content: 6.97 wt %) was obtained.

The silver content of the crosslinked CMC(Ag) obtained was measured with the ammonium thiocyanate determination method.

As a result, the silver content was 0.115 wt % (for anhydride) and 0.107 wt % (for water-containing specimen), and the degree of substitution to silver was 0.0028.

The specimens obtained in Examples 1–9 were tested for (a) heat stability and (b) light stability. The results are shown in Table 1.

(a) Heat stability test

A small amount of each specimen was put in a micro-tube and heated at 105° C. for 72 hours in an oven. The specimen after heating was compared with the one before heating for color tone.

(b) Light stability test

A small amount of each specimen was put in a micro-tube and exposed to sunlight through a window glass for 20 days. The specimen after heating was compared with the one before heating for color tone.

COMPARATIVE EXAMPLE 1

Preparation of crosslinked CMC(Ag) (DS=0.53, silver content=18.63 wt %)

3.6367 g of crosslinked CMC(Na) (DS=0.53, water content: 12.6 wt %) was suspended in 250 ml of water. A silver nitrate solution ($AgNO_3$:water=1.4167 g/50 ml) was added to the suspension, which was shaked for 19 hours under light shielded.

The precipitate was filtered with a glass filter, washed with a 50% ethanol and then with a 100% ethanol and dried with $P_2O_5$+silica gel for three days. 4.0202 g of crosslinked CMC(Ag) (water content: 5.028 wt %) was obtained.

The silver content of the crosslinked CMC(Ag) obtained was measured with the ammonium thiocyanate determination method.

As a result, the silver content was 18.63 wt % (for anhydride) and 17.68 wt % (for water-containing specimen).

COMPARATIVE EXAMPLE 2

Preparation of water-insoluble CMC(Ag) (DS=0.12, silver content=4.973 wt %)

3.6299 g of CMC(Na) (DS=0.12, water content: 10.73 wt %) was suspended in 200 ml of water. A silver nitrate solution ($AgNO_3$:water=0.414 g/10 ml) was added to the suspension, which was shaked for 19 hours under light shielded.

The precipitate was filtered with a glass filter, washed with a 50% ethanol and then with a 100% ethanol and dried with $P_2O_5$+silica gel for three days. 3.5099 g of water-insoluble crosslinked CMC(Ag) (water content: 3.96 wt %) was obtained.

The silver content of the water-insoluble CMC(Ag) obtained was measured with the ammonium thiocyanate determination method.

As a result, the silver content was 4.973 wt % (for anhydride) and 4.775 wt % (for water-containing specimen).

COMPARATIVE EXAMPLE 3

Preparation of water-insoluble CMC(Ag) (DS=0.10, silver content=0.064 wt %)

To 23.81 g of cellulose (CF-11, Whatman, water content 5.09 wt %), were added sodium hydroxide solution (NaOH:water=38 g/86 ml) and monochloro-acetic acid (0.12 g was dissolved in 20 ml of water). The mixture was stirred at 70° C. for one hour and then neutralized with 54 ml of acetic acid. After adding water, the mixture was subjected to centrifugal separation.

The residue was washed with water and made to acidic with 1N hydrochloric acid.

The separate residue was washed with water and then ethanol. The humid substance obtained was adjusted to pH 10 by dripping sodium hydroxide solution (1 g/50 ml) while stirring. The insoluble portion was centrifugally separated, washed with 50% ethanol and then 100% ethanol, and dried under vacuum to obtain a water-insoluble CMC(Na).

5.7006 g of water-insoluble CMC(Na) (DS=0.10, water content: 12.29 wt %) was suspended in 100 ml of water. A silver nitrate solution ($AgNO_3$:water=5.17 mg/10 ml) was added to the suspension, which was shaked for 68 hours under light shielded.

The precipitate was filtered with a glass filter, washed with a 50% ethanol and then with a 100% ethanol and dried with $P_2O_5$+silica gel for three days. 5.5207 g of water-insoluble CMC(Ag) (water content: 8.45 wt %) was obtained.

The silver content of the water-insoluble CMC(Ag) obtained was measured with the ammonium thiocyanate determination method.

As a result, the silver content was 0.064 wt % (for anhydride) and 0.059 wt % (for water-containing specimen).

The Comparative Examples 1–3 were tested for (a) heat stability and (b) light stability. The results are shown in Table 1.

The Table shows that for Examples 1–9 the specimen that was white before testing turned light yellow or yellow or remained white. In contrast, for Comparative Examples 1–3, in which the silver content or the DS value was not within the desired ranges, the specimens showed browning remarkably.

EXAMPLE 10

Preparation of water-soluble CMC(Ag) (DS=0.56, silver content=0.010 wt %)

53.25 g of CMC(Na) (DS=0.56, water content: 6.17 wt %) was suspended in 1000 ml of 80% methanol. A silver nitrate solution ($AgNO_3$:water=127 mg/25 ml) was added to the suspension, which was shaked for 144 hours under light shielded.

The precipitate was filtered with a glass filter, washed with a 80% ethanol and then with a 100% ethanol and dried with $P_2O_5$+silica gel for three days. 36.9879 g of water-soluble CMC(Ag) (water content: 9.50 wt %) was obtained.

The silver content of the water-soluble CMC(Ag) obtained was measured with the ammonium thiocyanate determination method.

As a result, the silver content was 0.010 wt % (for anhydride) and 0.009 wt % (for water-containing specimen).

EXAMPLE 11

Preparation of crosslinked CMC(Ag) (DS=0.53, silver content=1.00 wt %)

3.64 g of crosslinked CMC(Na) (DS=0.53, water content: 12.6 wt %) was suspended in 250 ml of water in a 500 ml graduated flask. A silver nitrate solution ($AgNO_3$:water=76 mg/50 ml) was added to the suspension, which was shaked for 19 hours under light shielded.

The precipitate was filtered with a glass filter, washed with a 50% ethanol and then with a 100% ethanol and dried with $P_2O_5$+silica gel for three days. 4.050 g of crosslinked CMC(Ag) (water content: 6 wt %) was obtained.

The silver content of the water-soluble CMC(Ag) obtained was measured with the ammonium thiocyanate determination method.

As a result, the silver content was 1.00 wt % (for anhydride) and 0.94 wt % (for water-containing specimen).

EXAMPLE 12

Preparation of CMC(Ag) (DS=0.4, silver content=0.045 wt %)

12.04 g of CMC(Na) (DS=0.4, water content: 8.81 wt %) was suspended in 250 ml of 80% methanol. A silver nitrate solution ($AgNO_3$:water=8.34 mg/5 ml) was added to the suspension, which was shaked for 137 hours under light shielded.

The precipitate was filtered with a glass filter, washed with a 80% methanol and then with a 100% methanol and dried with $P_2O_5$+silica gel for three days. 11.747 g of CMC(Ag) (water content: 11.27 wt %) was obtained.

The silver content of the CMC(Ag) obtained was measured with the ammonium thiocyanate determination method.

As a result, the silver content was 0.045 wt % (for anhydride) and 0.040 wt % (for water-containing specimen).

COMPARATIVE EXAMPLE 4

To a monomer compound consisting of 50 g of styrene, 40 g of ethylacrylate, 9 g of acrylic acid and 2 g of divinylbenzene (containing 45 wt % ethylvinylbenzene and diethylbenzene), 150 g of aqueous solution containing 0.75 g of ammonium persulfate and 7.5 g of emulsifier (NOIGEN EA 160, Daiichi Kogyo Seiyaku Co., Ltd.) was dripped to disperse. Polymerization was started at 70° C. while stirring the mixture in nitrogen atmosphere and maintained for five hours. A white precipitate was formed when the reaction was complete. It was filtered by centrifugal separation, washed with water and then ethanol, and vacuum dried. This produced 118.24 g (water content 6.49 wt %) of polyacrylic acid copolymer.

To 10.41 g (dry weight: 9.747 g) of the polyacrylic acid copolymer obtained, a silver nitrate solution ($AgNO_3$:water=3.098 g/60 ml) was added and the mixture was shaked for one hour under light shielded.

The precipitate was filtered with a glass filter, washed with a 80% methanol and then with a 100% methanol and dried with $P_2O_5$+silica gel for three days. 7.2241 g of compound (water content: 27.165 wt %) was obtained.

COMPARATIVE EXAMPLE 5

To 10 g (dry weight: 9.36 g) of the polyacrylic acid copolymer, 3.6% silver nitrate solution ($AgNO_3$:water=1.49 g/40 ml) was added. The mixture was shaked for 40 minutes under light shielded.

The precipitate was filtered with a glass filter, washed with a 80% methanol and then with a 100% methanol and dried with $P_2O_5$+silica gel for three days. 8.2174 g of compound (water content: 40.311 wt %) was obtained.

COMPARATIVE EXAMPLE 6

To 10 g (dry weight: 9.36 g) of the polyacrylic acid copolymer used in the Comparative Example 4, 0.4% silver nitrate solution ($AgNO_3$:water=0.144 g/40 ml) was added. The mixture was shaked for 80 minutes under light shielded.

The precipitate was filtered with a glass filter, washed with a 80% methanol and then with a 100% methanol and dried with $P_2O_5$+silica gel for three days. 4.483 g of compound (water content: 4.67 wt %) was obtained.

For the specimens obtained in Examples 2, 3, 6, 7, 10–12, Comparative Examples 1, 3, 4–6, antibacterial tests were performed. Table 2 shows the results of the tests.

(c) Antibacterial Test Method

Tests were carried out at 30° C. by use of phosphate buffer under the Shake Flask Method prescribed by Association of Antibacterial Treatments for Textiles, Japan. The test conditions are as follows: Shaking speed: 180±10 rpm, Shaking time: 1 hour, the bacteria used: *Staphylococcs aureus* (IFO 12732); silver concentration: 12.5 ng/ml. It was confirmed that all the specimens containing silver showed 100% sterilization ratio with the final silver concentration of 100 ng/ml or more.

As will be seen from Table 2, in Comparative Examples 1 and 3 in which the DS value or silver content were not within the desired ranges or Comparative Examples 4–6 in which the high polymers were other than CMC, the sterilization ratio was less than 40%.

In contrast, all the specimens of the Examples meeting all the requirements showed a sterilization ratio not less than 40%, which means excellent antibacterial property. Also, the results of Examples 2 and 6 show that if CMC has the DS value and the silver content in the desired ranges, the antibacterial agent would exhibit high sterilization ratio irrespective of whether CMC is crosslinked or not.

In the antibacterial property test, the sterilization ratio was determined with the silver concentration of 12.5 ng/ml. This was because the antibacterial effect of silver nitrate almost disappears at the silver concentration indicated above. Thus, it is considered that sterilization ratio shown in Table 2 is not the antibacterial effect by free silver ions, but that by fixed silver ions that do not elute.

COMPARATIVE EXAMPLE 7

The concentration of silver nitrate was adjusted to give the silver contents (µg/g) indicated in Table 3.

COMPARATIVE EXAMPLE 8

The concentration of zedite ion-exchanted by silver and copper ion (BACTEKILLER, KANEBO) was adjusted to give the silver content (µg/g) indicated in Table 3.

For the specimens of the Example 2 and Comparative Examples 7 and 8, the fungus resistance test was carried out. The results are shown in Table 3.

(d) Fungus resistance test

Filter paper was disintegrated with distilled water and the antifungal agent (Example 2 or Comparative Examples 7 and 8) was mixed. Paper was made from the mixture. The paper was cut into a size 50 mm square. The specimen thus obtained was tested under TAPPI Standard T-487 pm85 prescribed by Technical Association of the Pulp and Paper Industry, USA.

Inorganic salt agar medium mixed with 0.5% dextrose as a nutrient for fungus was used. As the test fungus, *Aspergillus niger* (TUA 234) was used. Culture was carried out for 14 days. The test results were evaluated in terms of the following three categories:
Evaluation mark
2: Area where hypha grows exceeds one third of the total area
1: The area does not exceed one third
0: The growth of hypha is not observed From Table 3, it is apparent that the specimens for Comparative Examples 7 and 8 do not show satisfactory antifungal property even if the silver content is as much as 10 µg/ml whereas the specimen for Example 2, which contains crosslinked CMC(Ag) and meets the requirements, show remarked antifungal property with silver content of 10 µg/g.

In order to examine the safety and stability for Example 1 and Comparative Example 1, they were tested for elution of silver.

(e) Silver elution test

The specimen was weighed so that the silver concentration in 10 ml will be 10 µg/ml. It was suspended in 10 ml of distilled water or phosphate buffer, the same as the one used in the antibacterial property test. The suspension was shaked at 31 C. at 180 rpm for one hour. After filtering, the concentration of silver that eluted into the solution was determined with the atomic absorption spectroscopy.

The results are shown in Table 4.

Table 4 shows that Comparative Example 1, which is a high silver substitution product, shows low elution in distilled water but high elution (40%) in phosphate buffer. This means that its safety and stability are not satisfactory.

In contrast, Example 1, which is a low silver substitution product, showed extremely low elution (1% or less) both in distilled water and phosphate buffer. This means that it has excellent safety and stability.

The antimicrobial agent of the present invention contains silver salt of carboxymethylcellulose having the degree of substitution to carboxymethyl group and the silver content restricted to specific ranges. This improves affinity with fiber and inhibits the elution of silver ions contained. It exhibits good sterilization ratio by contact of silver and microbial cells.

Also, it exhibits excellent stability to heat and light and its substrate little changes in color or quality.

If crosslinked CMC is used, the antimicrobial agent is insoluble to water and has good water resistance. Thus, it can continue antimicrobial property in applications where it contacts with water.

TABLE 1

|  | Crosslinkage | DS value | Water solubility | Color tone | Silver content (wt %)* | Heat stability test result | Light stability test result |
|---|---|---|---|---|---|---|---|
| Example |  |  |  |  |  |  |  |
| 1 | + | 0.53 | Insoluble | White | 0.048 | White | Light yellow |
| 2 | + | 0.53 | Insoluble | White | 0.048 | White | White |
| 3 | + | 0.51 | Insoluble | White | 0.114 | Light yellow | Yellow |

TABLE 1-continued

|   | Crosslinkage | DS value | Water solubility | Color tone | Silver content (wt %)* | Heat stability test result | Light stability test result |
|---|---|---|---|---|---|---|---|
| 4 | + | 0.60 | Insoluble | White | 0.067 | White | Light yellow |
| 5 | − | 0.56 | Soluble | White | 0.479 | Light yellow | Yellow |
| 6 | − | 0.56 | Soluble | White | 0.048 | White | White |
| 7 | + | 1.35 | Insoluble | White | 0.048 | White | Yellow |
| 8 | + | 1.35 | Insoluble | White | 0.040 | White | Yellow |
| 9 | + | 1.35 | Insoluble | White | 0.115 | White | Yellow |
| Comparative Example | | | | | | | |
| 1 | + | 0.53 | Insoluble | Light brown | 18.68 | Dark brown | Dark brown |
| 2 | − | 0.12 | Insoluble | Light brown | 4.973 | Dark brown | Brown |
| 3 | − | 0.10 | Insoluble | White | 0.064 | Light brown | Yellow |

*Anhydride

TABLE 2

|   | Crosslinkage | DS value | Water solubility | Silver content (wt %)* | Number of microbial cell Before shaking | Number of microbial cell After shaking | Sterilization ratio (%) |
|---|---|---|---|---|---|---|---|
| Example | | | | | | | |
| 2 | + | 0.53 | Insoluble | 0.048 | $1.1 \times 10^4$ | $3.0 \times 10^3$ | 72.7 |
| 3 | + | 0.51 | Insoluble | 0.114 | $1.1 \times 10^4$ | $3.5 \times 10^3$ | 68.2 |
| 6 | − | 0.56 | Soluble | 0.048 | $1.1 \times 10^4$ | $1.5 \times 10^3$ | 86.4 |
| 7 | + | 1.35 | Insoluble | 0.048 | $1.1 \times 10^4$ | $5.4 \times 10^3$ | 50.9 |
| 10 | − | 0.56 | Soluble | 0.01 | $1.1 \times 10^4$ | $5.3 \times 10^3$ | 48.2 |
| 11 | + | 0.53 | Insoluble | 1.00 | $1.1 \times 10^4$ | $4.8 \times 10^3$ | 41.8 |
| 12 | − | 0.4 | Soluble | 0.045 | $1.1 \times 10^4$ | $6.1 \times 10^3$ | 55.5 |
| Comparative Example | | | | | | | |
| 1 | + | 0.53 | Insoluble | 18.68 | $1.1 \times 10^4$ | $9.4 \times 10^3$ | 14.6 |
| 3 | − | 0.10 | Insoluble | 0.064 | $1.1 \times 10^4$ | $7.3 \times 10^3$ | 33.6 |
| 4 | − | — | Insoluble | 1.32 | $1.1 \times 10^4$ | $9.9 \times 10^3$ | 10.0 |
| 5 | − | — | Insoluble | 0.61 | $1.1 \times 10^4$ | $8.9 \times 10^3$ | 19.1 |
| 6 | − | — | Insoluble | 0.25 | $1.1 \times 10^4$ | $8.4 \times 10^3$ | 23.6 |
| Blank | — | — | — | — | $1.1 \times 10^4$ | $1.2 \times 10^4$ | −9.1 |
| Silver nitrate | — | — | — | — | $1.1 \times 10^4$ | $8.3 \times 10^3$ | 24.6 |

*Anhydride

TABLE 3

|   | Silver content (μg/g) | Evaluation mark |
|---|---|---|
| Example 2 Crosslinked CMC(Ag) | 0.0 | 2 |
|  | 2.5 | 2 |
|  | 5.1 | 2 |
|  | 10.0 | 0 |
|  | 20.0 | 0 |
|  | 39.9 | 0 |
| Comparative Example 7 Silver nitrate | 0.0 | 2 |
|  | 2.5 | 2 |
|  | 5.0 | 2 |
|  | 10.0 | 2 |
|  | 20.0 | 0 |
|  | 40.0 | 0 |
| Comparative Example 8 | 0.0 | 2 |
|  | 2.6 | 2 |
|  | 5.1 | 2 |
| Zeolite ion-exchanged by silver and copper ion | 10.3 | 2 |
|  | 20.5 | 0 |
|  | 41.0 | 0 |

TABLE 4

| | DS value | Silver content (wt %) | Test solution | Concentration of silver added (μg/ml) | Concentration of silver eluted (μg/ml) | Elution ratio (%) |
|---|---|---|---|---|---|---|
| Example 1 | 0.53 | 0.048 | Distilled water | 10.0 | <0.1 | <1 |
| | | | Phosphate buffer | 10.1 | 0.10 | 1.0 |
| Comparative Example 1 | 0.53 | 18.68 | Distilled water | 9.6 | 0.15 | 1.6 |
| | | | Phosphate buffer | 10.0 | 4.07 | 40.7 |

What is claimed is:

1. An antimicrobial agent comprising a silver salt of carboxymethylcellulose of formula

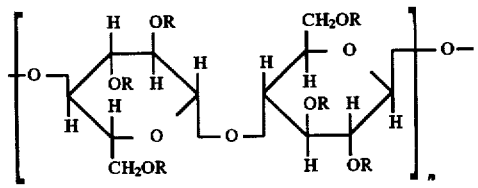

wherein R is H or a carboxymethyl group which is selected from the group of $CH_2COOH$ and $CH_2COOM$ wherein M is an alkali metal, and n is 100–2000;
wherein R is H and not a carboxyl group to the extent that the degree of substitution is not less than 0.4, and
wherein H in $CH_2COOH$ or M in $CH_2COOM$ is replaced with silver to the extent necessary to provide a compound with a silver content of 0.01 to 1% by weight.

2. The antimicrobial agent as claimed in claim 1 wherein the degree of substitution to carboxymethyl group is 0.4 to 1.

3. The antimicrobial agent as claimed in claim 1 wherein said carboxymethylcellulose is a crosslinked, water-insoluble compound.

4. The antimicrobial agent as claimed in claim 2 wherein said carboxymethylcellulose is a crosslinked, water-insoluble compound.

5. A method of providing an antimicrobial effect to materials comprising adding a compound of formula 1

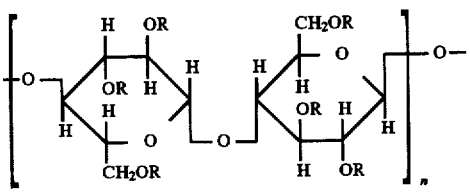

wherein R is H or a carboxymethyl group which is selected from the group of $CH_2COOH$ and $CH_2COOM$ wherein M is an alkali metal, and n is 100–2000;
wherein R is H and not a carboxyl group to the extent that the degree of substitution is not less than 0.4, and
wherein H in $CH_2COOH$ or M in $CH_2COOM$ is replaced with silver to the extent necessary to provide a compound with a silver content of 0.01 to 1% by weight, to said materials.

6. The method of claim 5 wherein the materials are selected from the group consisting of fibrous products, paper, leather and porous material.

7. The method of claim 5 wherein the method achieves a sterilization ratio over 40%.

8. The method of claim 5 wherein the compound of formula 1 is dissolved or suspended in a binder, applied to the product to be protected from bacteria or fungus, and the binder removed.

9. The method of claim 5 wherein the materials are impregnated with the compound of formula 1 in a solvent and the solvent removed, or the compound is mixed with wood pulp or cellulose fiber and paper made.

* * * * *